US011191586B2

(12) United States Patent
Alexander

(10) Patent No.: US 11,191,586 B2
(45) Date of Patent: *Dec. 7, 2021

(54) REMOVABLE TIP FOR USE WITH ELECTROSURGICAL DEVICES

(71) Applicant: Jamison Alexander, Denison, TX (US)

(72) Inventor: Jamison Alexander, Denison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/598,860

(22) Filed: Oct. 10, 2019

(65) Prior Publication Data

US 2021/0000531 A1 Jan. 7, 2021

Related U.S. Application Data

(63) Continuation-in-part of application No. 16/460,048, filed on Jul. 2, 2019.

(51) Int. Cl.
*A61B 18/14* (2006.01)
*A61B 18/00* (2006.01)

(52) U.S. Cl.
CPC .......... *A61B 18/14* (2013.01); *A61B 18/1402* (2013.01); *A61B 2018/00178* (2013.01); *A61B 2018/00589* (2013.01); *A61B 2018/00595* (2013.01); *A61B 2018/00601* (2013.01); *A61B 2018/1462* (2013.01)

(58) Field of Classification Search
CPC ...... A61B 18/1442; A61B 2017/00473; A61B 2017/2808; A61B 2018/00077; A61B 2018/00595; A61B 2018/00601; A61B 2018/00922; A61B 2018/0094; A61B 2018/00958; A61B 2018/1462; A61B 2017/305

See application file for complete search history.

(56) References Cited

U.S. PATENT DOCUMENTS

| 2,042,985 A | 6/1936 | Gardella |
| 3,465,621 A * | 9/1969 | Ladd ...................... A61B 17/30 |
| | | 294/99.2 |
| 4,418,692 A | 12/1983 | Guay |
| 4,657,016 A * | 4/1987 | Garito ................ A61B 17/3213 |
| | | 439/784 |

(Continued)

FOREIGN PATENT DOCUMENTS

| CN | 204233211 U | 4/2015 |
| WO | 2009036346 A2 | 3/2009 |

(Continued)

*Primary Examiner* — Jaymi E Della

(57) ABSTRACT

Disclosed herein are various embodiments of electrosurgical devices. In one embodiment a removable tip for use with an electrosurgical tool comprises a first tip member and a second tip member, each having a proximal end and a distal end; an actuator for moving the first and second tip members between a closed position where the distal ends of the first and second tip members are proximate one another, and an open position where the distal ends of the first and second tip members are separated by a distance from one another, wherein the actuator includes a first actuating member comprising a portion of the first tip member and a second actuating member comprising a portion of the second tip member; and an insertion member coupled with the proximal ends of the tip members for inserting the removable tip within an opening in the electrosurgical tool.

18 Claims, 14 Drawing Sheets

(56) References Cited

U.S. PATENT DOCUMENTS

| | | | |
|---|---|---|---|
| 5,352,235 A | 10/1994 | Koros et al. | |
| 5,752,951 A | 5/1998 | Yanik | |
| 5,766,167 A | 6/1998 | Eggers et al. | |
| 5,925,041 A | 7/1999 | Long et al. | |
| 6,371,956 B1 | 4/2002 | Wilson et al. | |
| 9,539,049 B2 | 1/2017 | Allen, IV et al. | |
| 9,763,685 B2 | 9/2017 | Batchelor et al. | |
| 2004/0193211 A1* | 9/2004 | Voegele | A61B 5/6838 606/205 |
| 2005/0137590 A1 | 6/2005 | Lawes et al. | |
| 2005/0240177 A1* | 10/2005 | Tabermejo, Jr. | A61B 18/1442 606/42 |
| 2006/0041257 A1 | 2/2006 | Sartor et al. | |
| 2006/0111613 A1 | 5/2006 | Boutillette et al. | |
| 2009/0012519 A1* | 1/2009 | Manrique | A61B 18/1442 606/51 |
| 2009/0209946 A1 | 8/2009 | Swayze et al. | |
| 2009/0299367 A1 | 12/2009 | Ginnebaugh et al. | |
| 2010/0063502 A1 | 3/2010 | Black et al. | |
| 2013/0178852 A1* | 7/2013 | Allen, IV | A61B 18/1442 606/42 |
| 2014/0135757 A1 | 5/2014 | Bernard et al. | |
| 2014/0276797 A1 | 9/2014 | Batchelor et al. | |
| 2015/0157386 A1 | 6/2015 | Bloom et al. | |
| 2015/0327910 A1* | 11/2015 | Brooke | A61B 17/30 606/52 |
| 2015/0327913 A1 | 11/2015 | Horner | |
| 2016/0038219 A1 | 2/2016 | Barry et al. | |
| 2016/0051273 A1 | 2/2016 | Batchelor et al. | |
| 2016/0058499 A1 | 3/2016 | Brooke | |
| 2017/0319264 A1 | 11/2017 | Haupt | |
| 2018/0036062 A1* | 2/2018 | Eladoumikdachi | A61B 18/14 |
| 2018/0042666 A1 | 2/2018 | Artale et al. | |
| 2021/0000533 A1 | 1/2021 | Alexander | |

FOREIGN PATENT DOCUMENTS

| | | |
|---|---|---|
| WO | 2017106602 A1 | 6/2017 |
| WO | 2017123468 A1 | 7/2017 |
| WO | 2021003332 A1 | 1/2021 |

\* cited by examiner

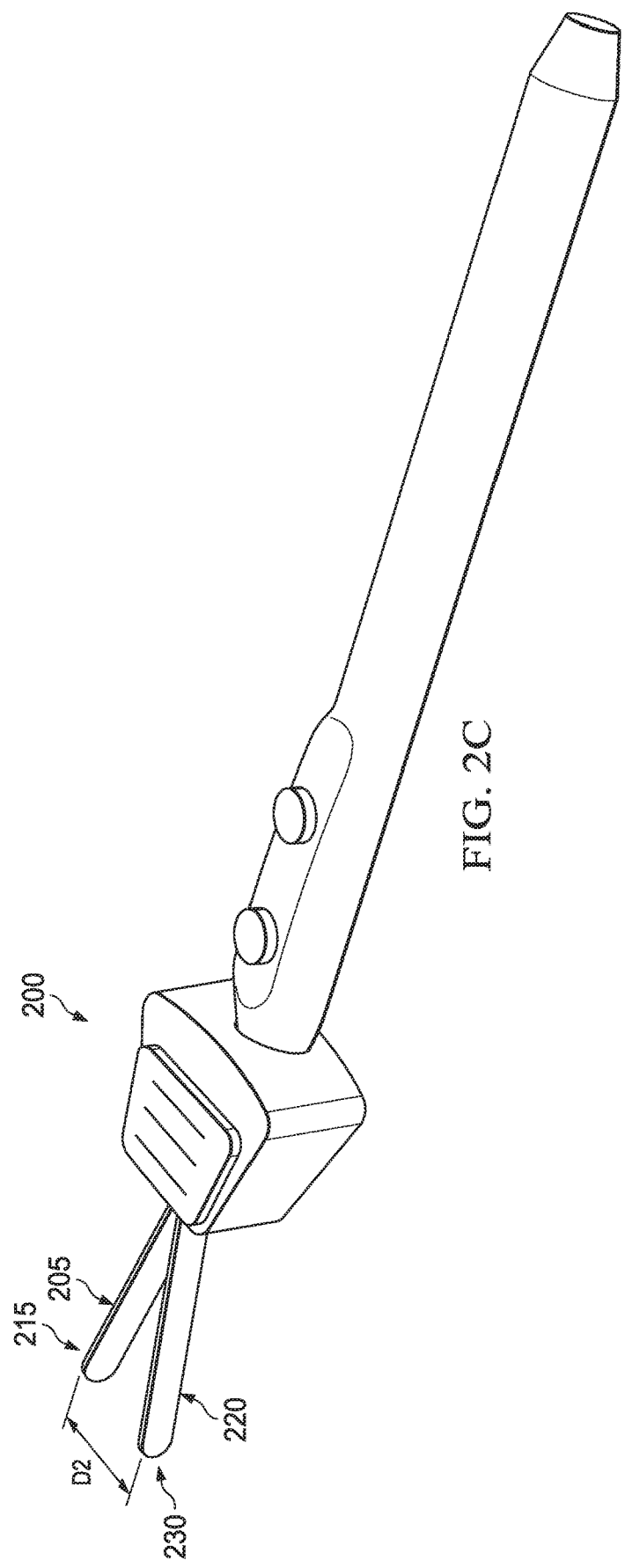

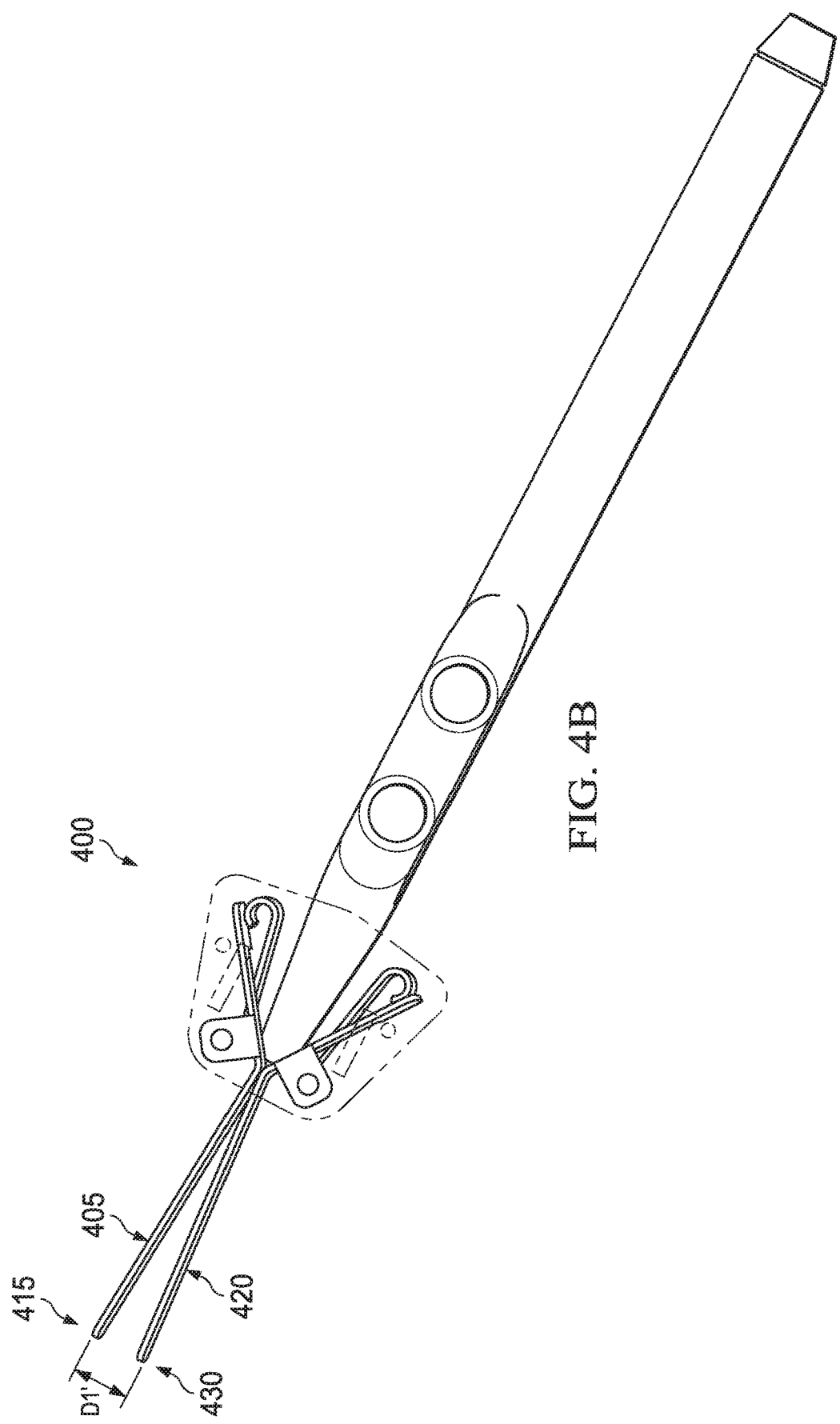

REMOVABLE TIP FOR USE WITH ELECTROSURGICAL DEVICES

CROSS-REFERENCE TO RELATED APPLICATION

This application is a continuation-in-part of U.S. application Ser. No. 16/460,048, filed by Jamison Alexander on Jul. 2, 2019, entitled "REMOVABLE TIP FOR USE WITH ELECTROSURGICAL DEVICES," commonly assigned with this application and incorporated herein by reference in its entirety.

TECHNICAL FIELD

This application is directed, in general, to surgical tools and, more specifically, to a removable tip which may be used with an electrosurgical tool for, among other things, cutting, clamping, and cauterizing tissue and vessels.

BACKGROUND

Electrosurgical devices use high-frequency electrical current to cut, coagulate, and cauterize tissue and vessels and are used in a wide array of surgical procedures. Electrosurgical devices are generally handheld devices guided by a surgeon, making it possible to apply a high-frequency energy to tissue. Electrosurgical devices may be used, for example, to cut tissue, or in other examples, to seal or cauterize tissue and vessels. The energy level may be adjusted by the surgeon by means of control switches disposed in some embodiments on the handheld device, such as, e.g. one or more buttons.

During an operation, the surgeon generally has to navigate through several layers of tissue and vessels and may need to cut some tissue or vessels, while sealing or cauterizing other tissue or vessels. For example, electrosurgical devices are commonly used during surgery in order to stop bleeding by using an alternating current directly to heat tissue and thereby reduce blood loss and/or improve surgical vision. In some procedures, there may be a limited amount of space available for surgical instruments. In some embodiments, additional forceps or instruments may be necessary to clamp tissue or clamp around a vessel in order to use an electrosurgical device thereon or navigate around the tissue or vessel due to its size and/or location. In some cases, the surgeon may need additional space within the surgical field or may require an additional hand or set of hands to maneuver the instruments. Such interruptions in the operation may add additional time for the procedure and pose additional risks to the patient.

BRIEF DESCRIPTION

Reference is now made to the following descriptions taken in conjunction with the accompanying drawings, in which:

FIG. 2C is a perspective view of the electrosurgical tool of FIG. 2A shown with the removable tip in a partially open configuration;

FIG. 4B is a perspective view of the electrosurgical tool of FIG. 4A shown with the removable tip in a partially open configuration;

DETAILED DESCRIPTION

Two primary types of electrosurgical device are known, namely bipolar and monopolar devices. In monopolar arrangements the electrosurgical device is provided with an active electrode and a return electrode is attached to the patient. The electric current flows from the active electrode into the body and returns through the return electrode (which is connected to a grounding circuit). The current density decreases rapidly with distance away from the electrode such that the heating of tissue is localized to the tip of the electrosurgical device. In bipolar devices, a pair of electrodes, for example the tips of forceps, are each connected to the supply circuit and no return electrode is required. When tissue is engaged by or proximal to the pair of electrodes, the high frequency electric current flows through the device and tissue providing a localized heating of the tissue.

Conventional electrosurgical devices may include a single member tip or may include a forceps design which is substantially based upon traditional surgical forceps. As such, a surgeon may have to change electrosurgical instruments, from a single tip to a forceps type design, depending on the function required during a procedure. As such, switching between conventional tips and forceps may add time and risk to a patient during a surgical procedure. In addition, conventional electrosurgical devices are not adjustable to adapt to various body cavity areas or depths and also have the ability to cut, clamp, and cauterize both tissue and vessels.

Figure 1:
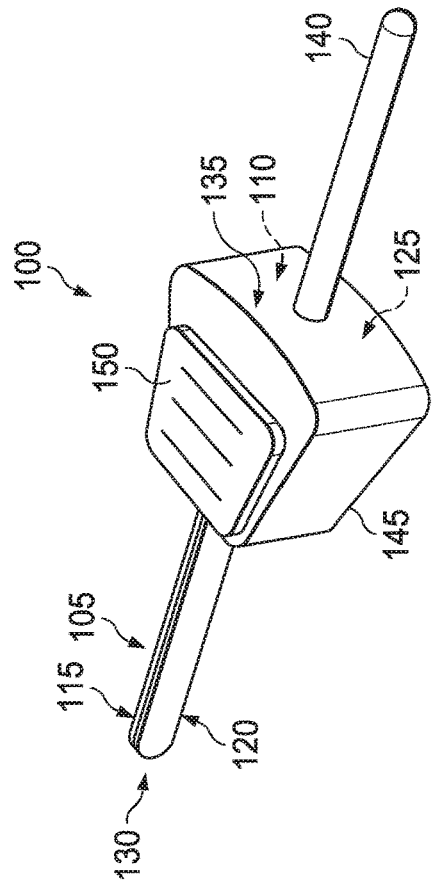
FIG. 1 is a perspective view of one embodiment of a removable tip for use with an electrosurgical device according to the present disclosure.
Figure 2A:
FIG. 2A is a perspective view of one embodiment of an electrosurgical tool according to the present disclosure, shown with a removable tip in a closed configuration.

Disclosed herein are embodiments of a removable tip for use with an electrosurgical tool which may be used in surgical procedures. Referring to the drawings, and more specifically, FIG. 1, there is shown a removable tip 100 representing one embodiment of the present disclosure. The removable tip 100 comprises a first tip member 105 having a proximal end 110 and a distal end 115. A second tip member 120 likewise has a proximal end 125 and a distal end 130. In some embodiments, at least one or both of the first tip member 105 and the second tip member 120 may include at least one electrically conductive surface near the distal ends 115 and 130 thereof. The first tip member 105 and second tip member 120 may be configured in some embodiments to move from a closed position (as shown in FIG. 1 and FIG. 2A) where the distal end 115 of the first tip member 105 and the distal end 130 of the second tip 120 member are proximate one another, and an open position where the distal end 115 of the first tip member 105 and the distal end 130 of the second tip member 120 are separated by a distance from one another. (Varying stages of open positions will be illustrated in FIGS. 2B-2D). In some embodiments, an actuator 135 may be coupled to the first tip member 105 and the second tip member 120 for moving the first and second tip members 105 and 120 between the closed position and one or more open positions.

In some embodiments, an insertion member 140 may be coupled with the proximal ends 110 and 125 of the first and second tip members 105 and 120, the insertion member 140 for inserting the removable tip 100 within an opening in an electrosurgical tool. In some embodiments, the insertion member 140 may be rotatable within the opening in the electrosurgical tool such that the removable tip 100 may be adjusted to varying angles with respect to the electrosurgical tool. By enabling adjustment of an angle of the removable tip, a surgeon may be able to better maneuver the removable tip 100 within a body cavity than conventional electrosurgical devices. In some examples, the removable tip 100 may need to be rotated to achieve a better placement in the body cavity while enabling the surgeon's hand to be placed in a better or more comfortable or maneuverable position.

In some embodiments, the removable tip 100 may include a housing 145 positioned between the distal ends 110 and 130 and the proximal ends 115 and 125 of the first and second tip members 105 and 120. In some embodiments, the actuator 135 may be positioned at least partially within the housing 145. In other embodiments, the housing 145 may be positioned at least partially over the insertion member 140.

In some embodiments, the actuator 135 may include a switch 150. The switch 150, in embodiments not including a housing 145, may be located in various locations on or about the actuator 135. The switch 150 may be configured to move linearly upon pressure applied by a finger or thumb and move the first and second tip members 105 and 120 between closed and open positions, and various positions in between.

In some embodiments, the actuator 135 may include one or more separating members, which may be positioned, in some embodiments within the housing 145. The one or more separating members may be positioned about or between the first and second tip members 105 and 120 for separating the distal ends 115 and 130 of the first and second tip members 105 and 120 when the surgeon engages the actuator 135, which in some embodiments, may be operation of the switch 150. The separating members may also act to move the distal ends 115 and 130 of the first and second tip members 105 and 120 closer together when the actuator 135 may be engaged again, in some embodiments, moving the switch 150 in a second direction.

The removable tip 100 may be adjusted between a closed position and varying open positions (examples shown in FIGS. 2A-2D) depending on what the surgeon may need to use the removable tip 100 for during a surgical procedure. In some examples, the removable tip 100 may need to be in a closed position, for example, when cutting tissue may be needed. However, in certain procedures, clamping the distal end 115 of the first tip member 105 and the distal end 130 of the second tip 120 about a vessel may be useful rather than using a second instrument to clamp around the vessel before applying current from a conventional electrosurgical tip, for example, for cutting or cauterizing a vessel.

The removable tip 100 may also accommodate varying lengths, both longer and shorter, of first tip members 105 and second tip members 120 such that the removable tip 100 may reach deeper within some body cavities without changing the entire electrosurgical tool, such as previously required with conventional fixed electrosurgical tools. In some embodiments, the first tip member 105 and second tip members 120 may be adjustable and/or extendable to varying lengths. In other embodiments, the insertion member 140 may also be adjustable and/or extended to varying lengths.

Referring now to FIGS. 2A through 2D illustrate another embodiment of a removable tip 200 shown coupled into an electrosurgical tool 270, shown in various stages. FIG. 2A illustrates the removable tip in a closed position, wherein distal ends 215 and 230 of first and second tip members 205 and 220 are proximate one another.

Figure 2B:
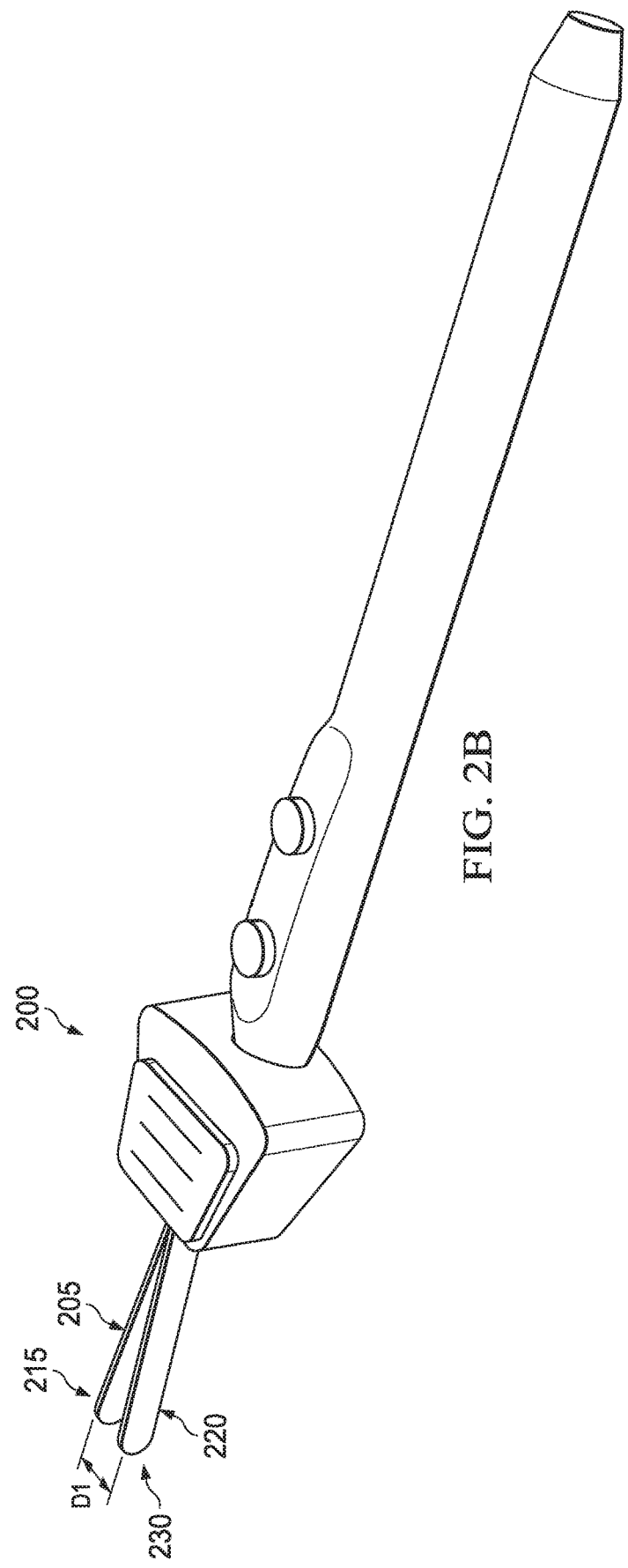
FIG. 2B is a perspective view of the electrosurgical tool of FIG. 2A shown with the removable tip in a starting to open configuration.
Figure 2D:
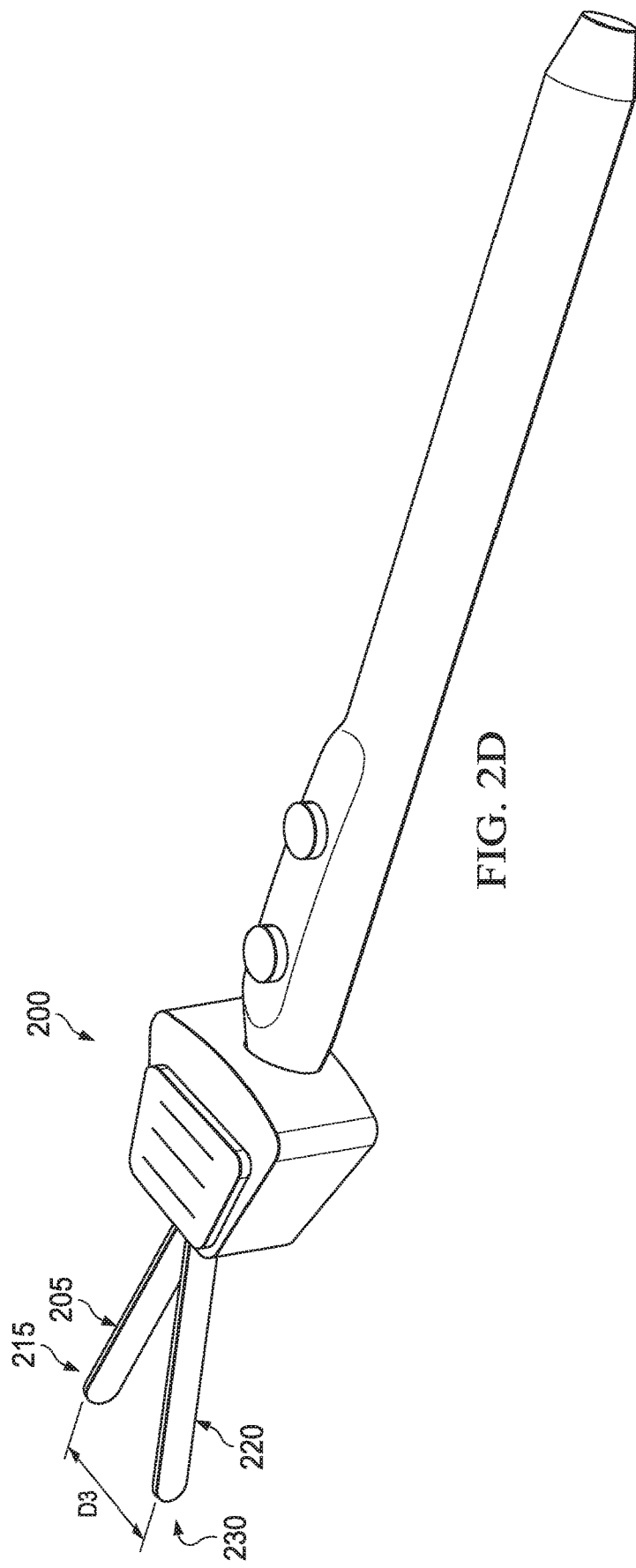
FIG. 2D is a perspective view of the electrosurgical tool of FIG. 2A shown with the removable tip in a fully open configuration.

FIGS. 2B through 2D illustrate the removable tip 200 in various open stages, wherein the distal ends 215 and 230 of the first and second tip members 205 and 220 are separated by various distances. FIG. 2B illustrates the removable tip 200 as the first and second tip members 205 and 220 are beginning to open and the distal ends 215 and 230 of the first and second tip members 205 and 220 begin to separate by a first distance D1. FIG. 2C illustrates the removable tip 200 in where the distal ends 215 and 230 first and second tip members 205 and 220 are separate by a second distance D2, which may be about halfway open, wherein halfway open is about 45-55% of fully open. FIG. 2D illustrates the removable tip 200 in a fully open position, where the distal ends 215 and 230 of first and second tip members 205 and 220 are separate by a third distance D3. Fully open, in this disclosure means the distal ends 215 and 230 of the first and second tip members 205 and 220 are within 95-100% open to the maximum functional separation of the distal ends 215 and 230 of the first and second tip members 205 and 220.

Referring again to FIG. 2A, the electrosurgical tool 270 includes a handheld electrosurgical unit 275. The handheld electrosurgical unit 275 may connect with a wall unit, in some embodiments via a plug-in connection such as a wire or cord. The wall unit may supply the electrical current to the electrosurgical tool 270. The first tip member 205 and second tip member 220 may include one or more conductive surfaces for conducting current to tissue to which it may be applied or clasped about. The handheld electrosurgical unit 275 may include, in some embodiments, at least a first button 280 to activate a cutting mode and a second button 285 to activate a cauterizing mode. Additional buttons or functions may be included in some embodiments of the handheld electrosurgical unit 275. Further, some embodiments of the removable tip 200 may be used in monopolar mode while others may be used in bipolar mode.

Figure 3:
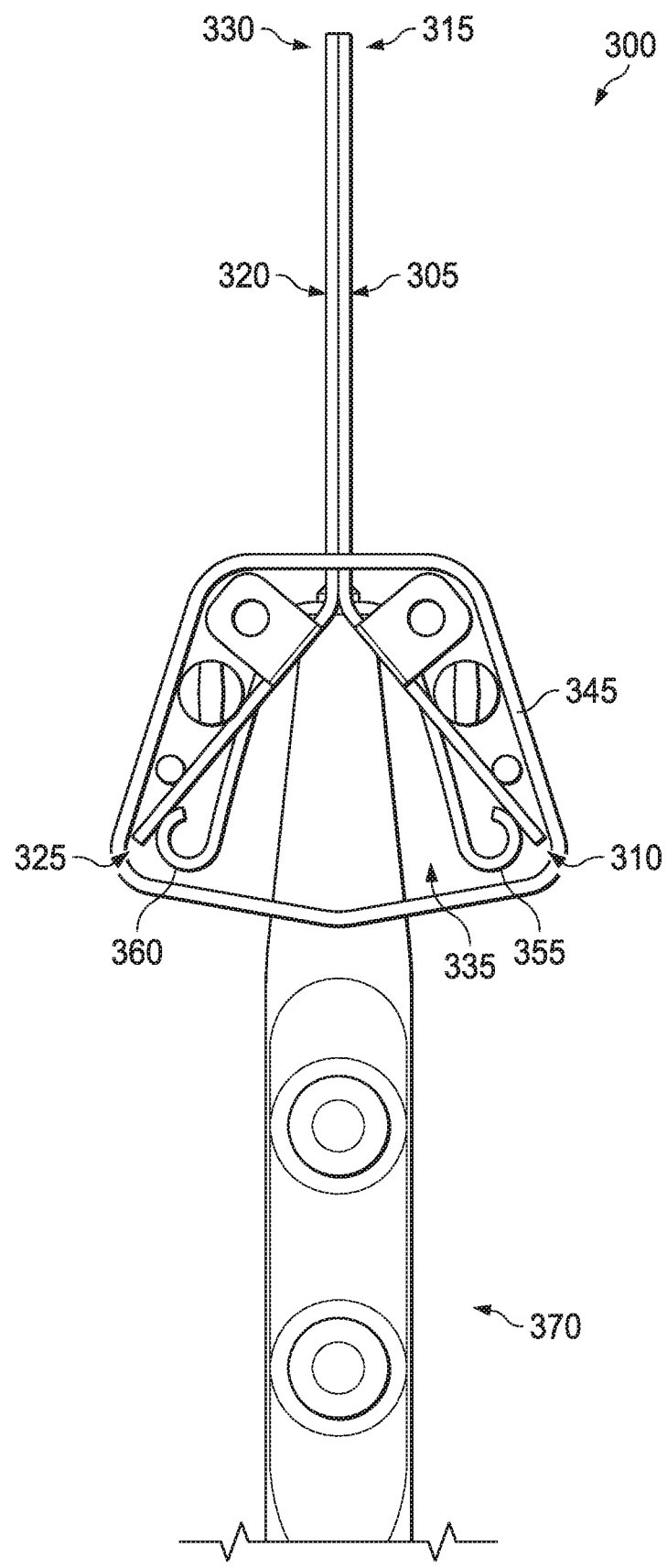
FIG. 3 is a partial sectional view of another embodiment of a removable tip for use with an electrosurgical device according to the present disclosure.

Referring now to FIG. 3, there is shown another embodiment of a removable tip 300 coupled into an electrosurgical tool 370 according to principles of the disclosure. The removable tip 300 may include a first tip member 305 having a proximal end 310 and a distal end 315. A second tip member 320 likewise has a proximal end 325 and a distal end 330. In some embodiments, at least one or both of the first tip member 305 and the second tip member 320 may include at least one electrically conductive surface near the distal ends 315 and 330 thereof. The first tip member 305 and second tip member 320 may be configured in some embodiments to move from a closed position to an open position, as discussed hereinabove and shown in FIG. 1 through FIG. 2D.

In some embodiments, an actuator 335 may be coupled to the first tip member 305 and the second tip member 320 for moving the first and second tip members 305 and 320 between the closed position and one or more open positions. The actuator 335 may, in some embodiments, be positioned within a housing 345. The view of FIG. 3 is a partial section-view, showing the inside of housing 345.

In some embodiments, the actuator 335 may include a first separating member 355 and a second separating member 360. In this embodiment, the first separating member 355 is adjacent the proximal end 310 of the first tip member 305 and the second separating member 360 is positioned adjacent the proximal end 325 of the second tip member 320, but the first separating member 355 and second separating member 360 may be positioned between the first and second tip members 305 and 320 at any location that enables the actuator to move the removable tip 300 between closed position and an open position. In another embodiment, the first separating member 355 and the second separating member 360 may be positioned at or incorporating into opposing ends of a single separating component.

Figure 4A:
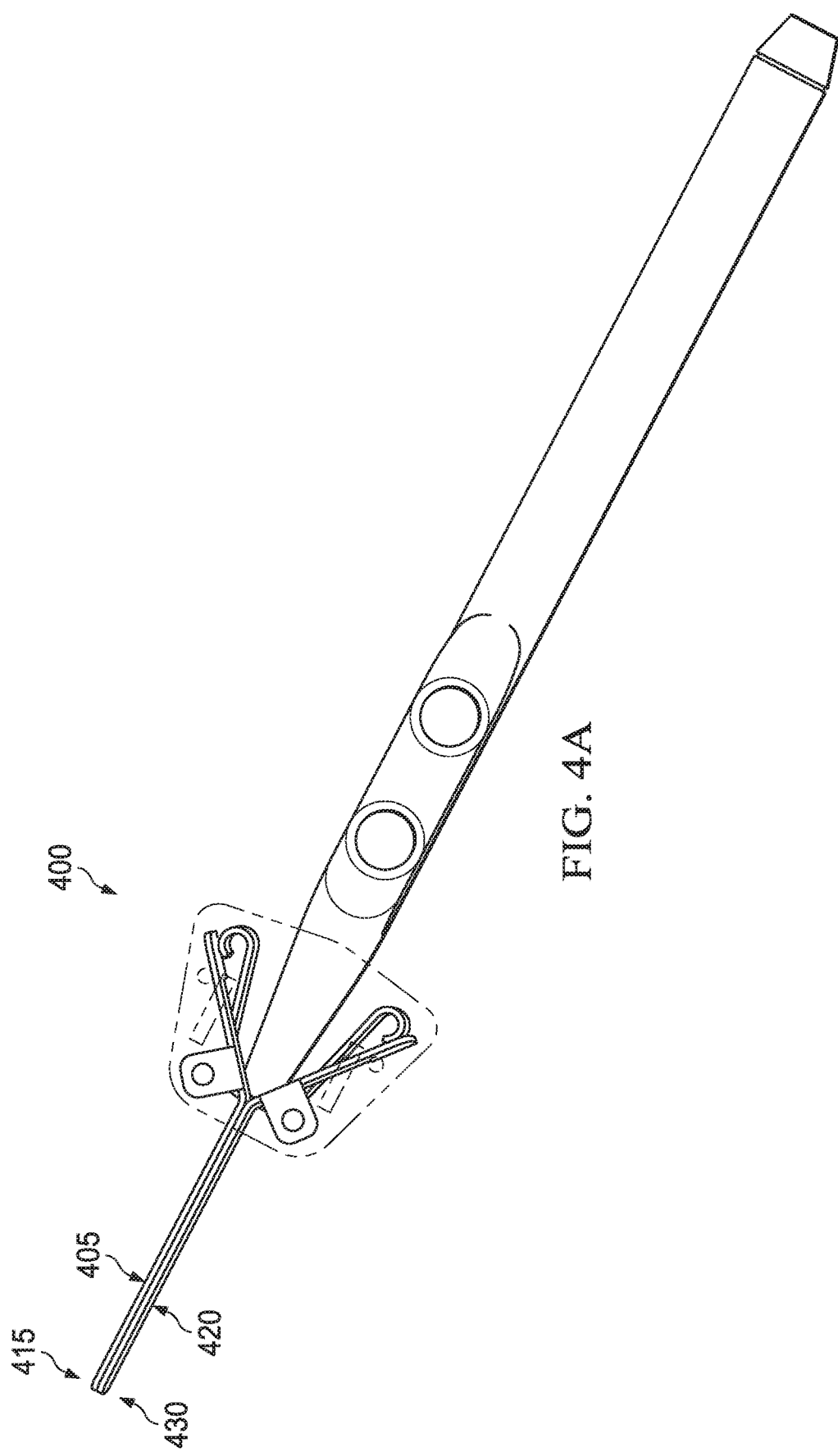
FIG. 4A is a perspective view of one embodiment of an electrosurgical tool according to the present disclosure, shown with a removable tip in a closed configuration.
Figure 4C:
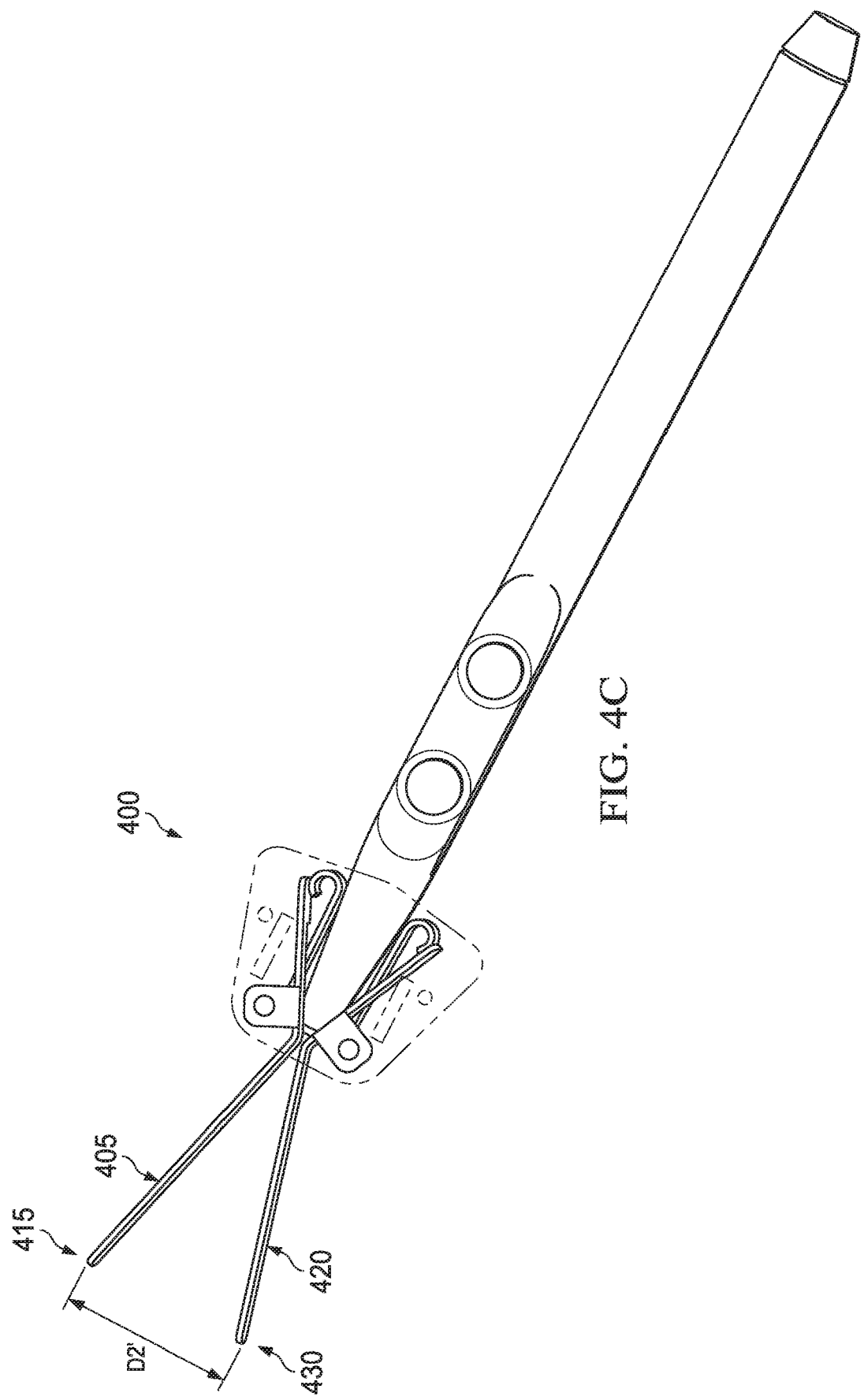
FIG. 4C is a perspective view of the electrosurgical tool of FIG. 4A shown with the removable tip in an open configuration.

Referring now to FIGS. 4A-4C, there is shown another embodiment of a removable tip 400 shown in 3 different positions: FIG. 4A shows the removable tip 400 in a closed position, wherein a distal end 415 of a first tip member 405 is proximate a distal end 430 of a second tip member 420. FIG. 4B illustrates the removable tip 400 in an opening position, wherein the distal ends 415 and 430 are separate by a distance D1'. FIG. 4C illustrates the removable tip 400 in an open position, wherein the distal ends 415 and 430 are separate by a distance D2'.

Figure 5A:
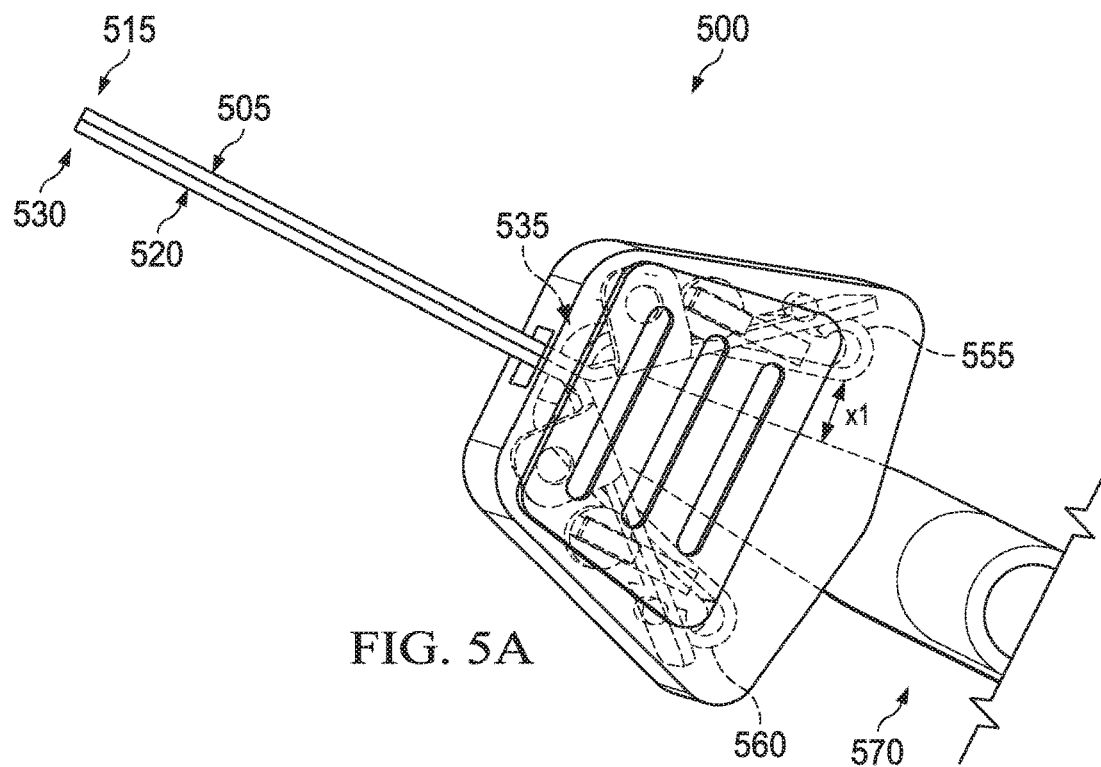
FIG. 5A is a perspective view of another embodiment of a removable tip for use with an electrosurgical device according to the present disclosure, shown with the removable tip in a closed configuration.
Figure 5B:
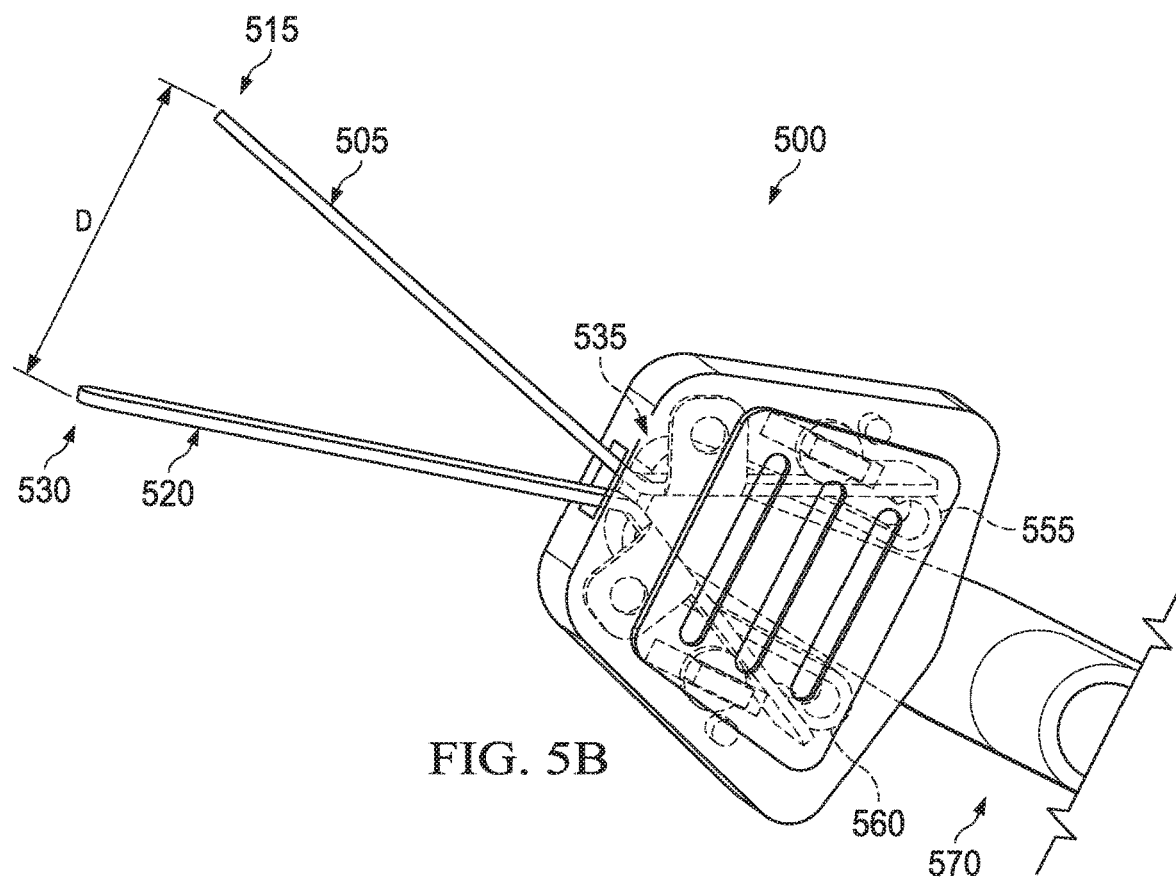
FIG. 5B is a perspective view of the removable tip shown in FIG. 5A, shown with the removable tip in an open configuration.

Referring now to FIGS. 5A and 5B there is shown another embodiment of a removable tip 500 shown in a closed position in FIG. 5A and an open position in FIG. 5B. As shown in FIG. 5A, in this embodiment, when the removable tip 500 is closed, a first separating member 555 and a second separating member 560 of an actuator 535 are each positioned at a distance x1 away from a distal end of an electrosurgical tool 570 onto which the removable tip 500 may be coupled. When the removable tip 500 is in an open position, the first and second separating members 555 and 560 may be proximate the distal end of the electrosurgical tool 570 such that there is little or no distance between the first and second separating members 555 and 560 and the distal end of the electrosurgical tool 570. When the removable tip 500 is in varying open positions, similar to those illustrated in FIG. 2B-2D, the distance between the first and second separating members 555 and 560 and the distal end of the electrosurgical tool 570 may vary accordingly.

Figure 6A:
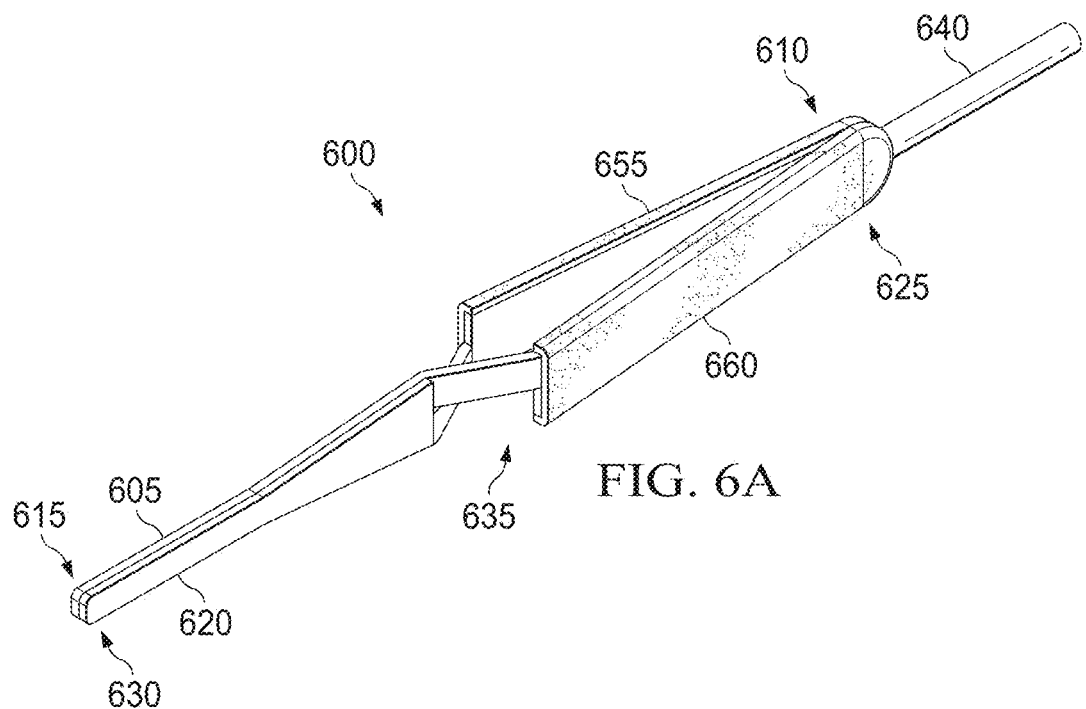
FIG. 6A is a perspective view of yet another embodiment of a removable tip for use with an electrosurgical device according to the present disclosure, shown with the removable tip in a closed configuration.
Figure 6B:
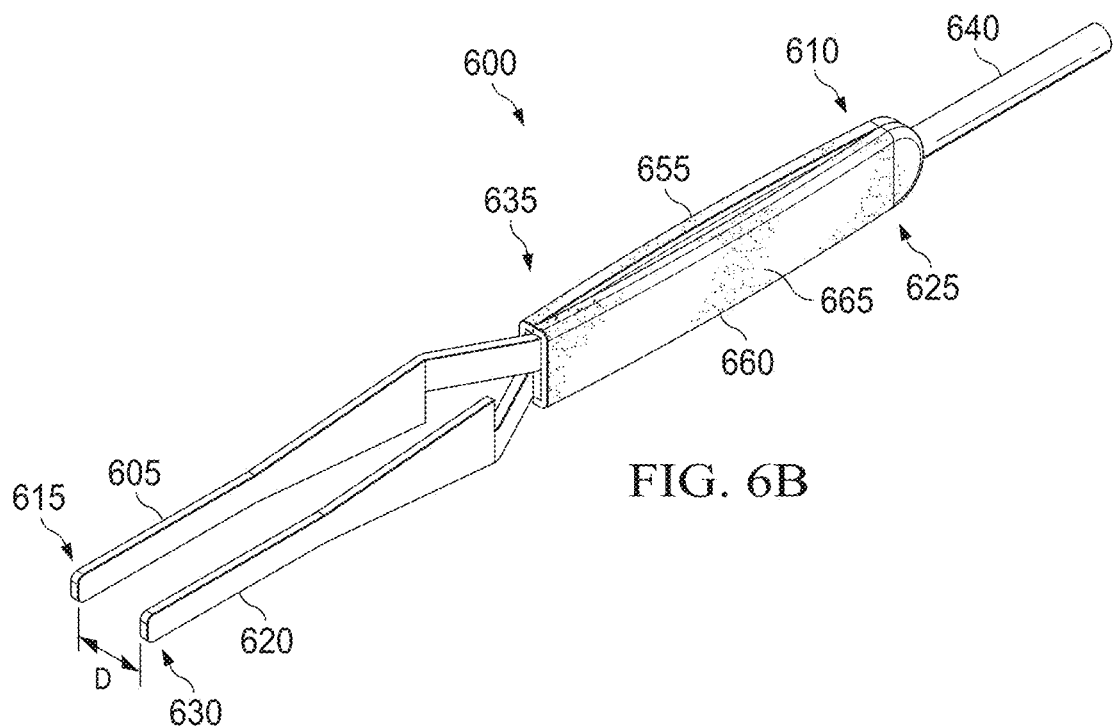
FIG. 6B is a perspective view of the removable tip shown in FIG. 6A, shown with the removable tip in an open configuration.
Figure 6C:
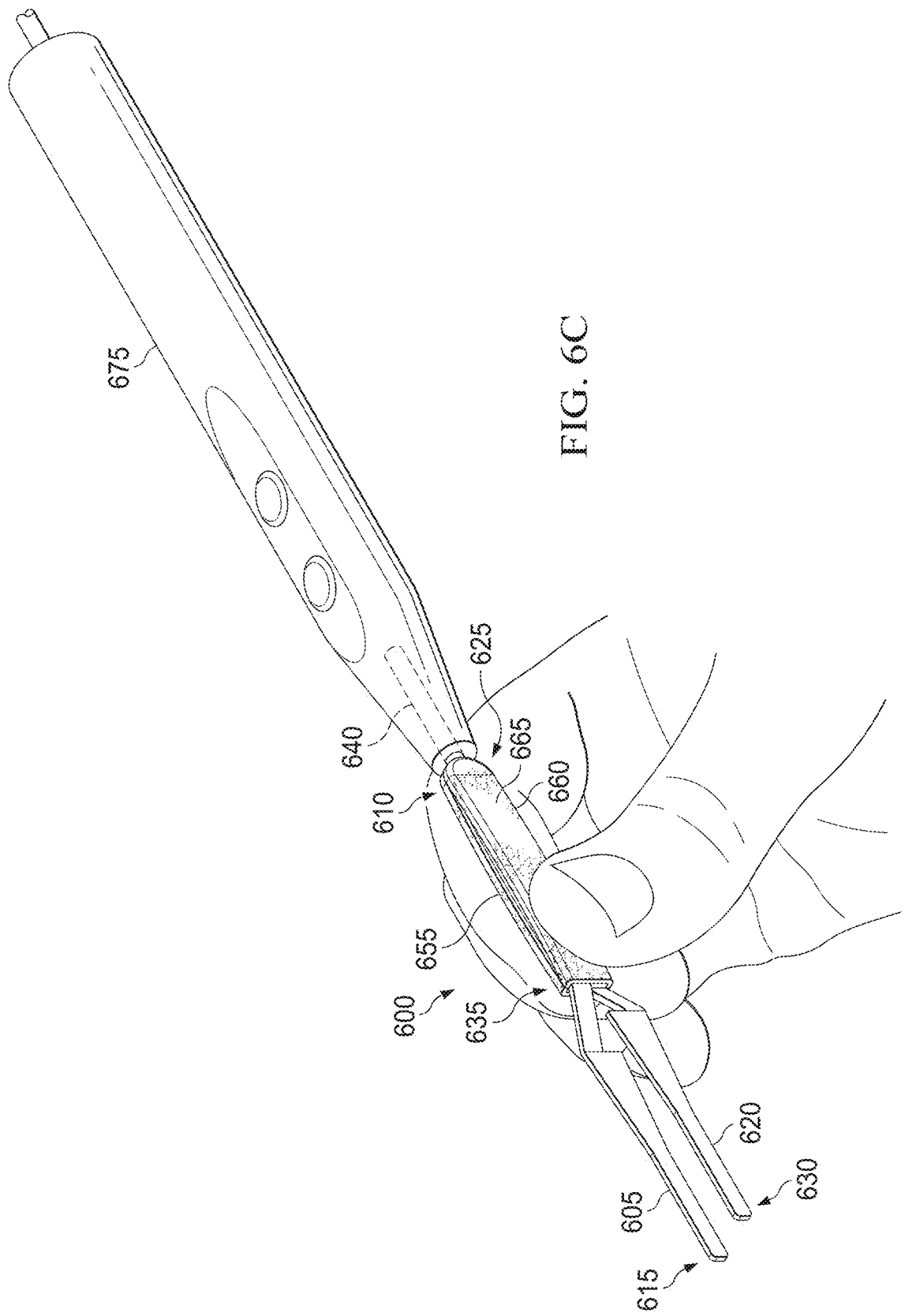
FIG. 6C is an environmental view of the removable tip shown in FIGS. 6A and 6B, shown with the removable tip in an open configuration.

Referring now to FIGS. 6A-6C, there is shown yet another embodiment of a removable tip 600 coupled into a handheld electrosurgical unit 675 according to principles of the disclosure. The removable tip 600 may include a first tip member 605 having a proximal end 610 and a distal end 615. A second tip member 620 likewise has a proximal end 625 and a distal end 630. In some embodiments, at least one or both of the first tip member 605 and the second tip member 620 may include at least one electrically conductive surface at or near the distal ends 615 and 630 thereof. The first tip member 605 and second tip member 620 may be configured in some embodiments to move from a closed position, as shown in FIG. 6A to an open position, as shown in FIG. 6B.

In some embodiments, an insertion member 640 may be coupled with the proximal ends 610 and 625 of the first and second tip members 605 and 620, the insertion member 640 for inserting the removable tip 600 within an opening in the handheld electro surgical unit 675. In some embodiments, the insertion member 640 may be rotatable within the opening in the electrosurgical unit 675 such that the removable tip 600 may be adjusted to varying angles with respect to the electrosurgical tool.

In some embodiments, an actuator 635 may be coupled to the first tip member 605 and the second tip member 620 for moving the first and second tip members 605 and 620 between the closed position and one or more open positions. In this embodiment, the actuator 635 comprises a portion of the first and second tip members 605 and 620.

In some embodiments, the actuator 635 may include a first separating member 655 and a second separating member 660. In one embodiment, the first separating member 655 and the second separating member 660 each comprise a portion of the first and second tip members 605 and 620. In some embodiments, to actuate the first and second tip members 605 and 610 from a closed position as shown in FIG. 6A to an open position shown in FIG. 6B, axial pressure may be applied to the first separating member 655 and the second separating member 660, moving the first separating member 655 and the second separating member 660 toward each other as the distal ends 615 and 630 move apart from one another. In some examples, the pressure may be applied to at least exterior surfaces of the first and second separating members 655 and 660.

In some embodiments, at least a portion of the first and second tip members 605 and 620 may be removable and/or replaceable. In one embodiment, the distal ends 615 and 630 may be removed at or above the first separating member 655 and the second separating member 660. The distal ends 605 and 620 may couple with the first separating member 655 and the second separating member 660 by a snap fit, tension fit, a locking fit, and other traditional coupling means for removing and replacing a distal end of a longitudinal member such as the first and second tip members 605 and 620.

Referring to FIG. 6C, there is shown an environmental view of the removable tip 600, shown with the actuator 635 engaged such that the distal ends 615 and 630 of the first and second tip members 605 and 620 are opened apart from each other. In this embodiment, the actuator 635 is shown engaged by fingers applying axial pressure to the first and second separating members 655 and 660. In one embodiment, the first separating member 655 and second separating member 660 may include a coating or covering 665 on at least an exterior surface of each, but in some embodiments, the coating or covering may cover or coat most or all surfaces of the first and second separating members 655 and 660. The coating 665 may comprise polymers, rubbers, plastics, and any other suitable material which may provide, in some embodiments, insulation from any electrical current running through the removable tip 600 and may also, in other embodiments, provide a non-slip grip, and/or comfort grip to a surgeon handling the removable tip 600.

Figure 7A:
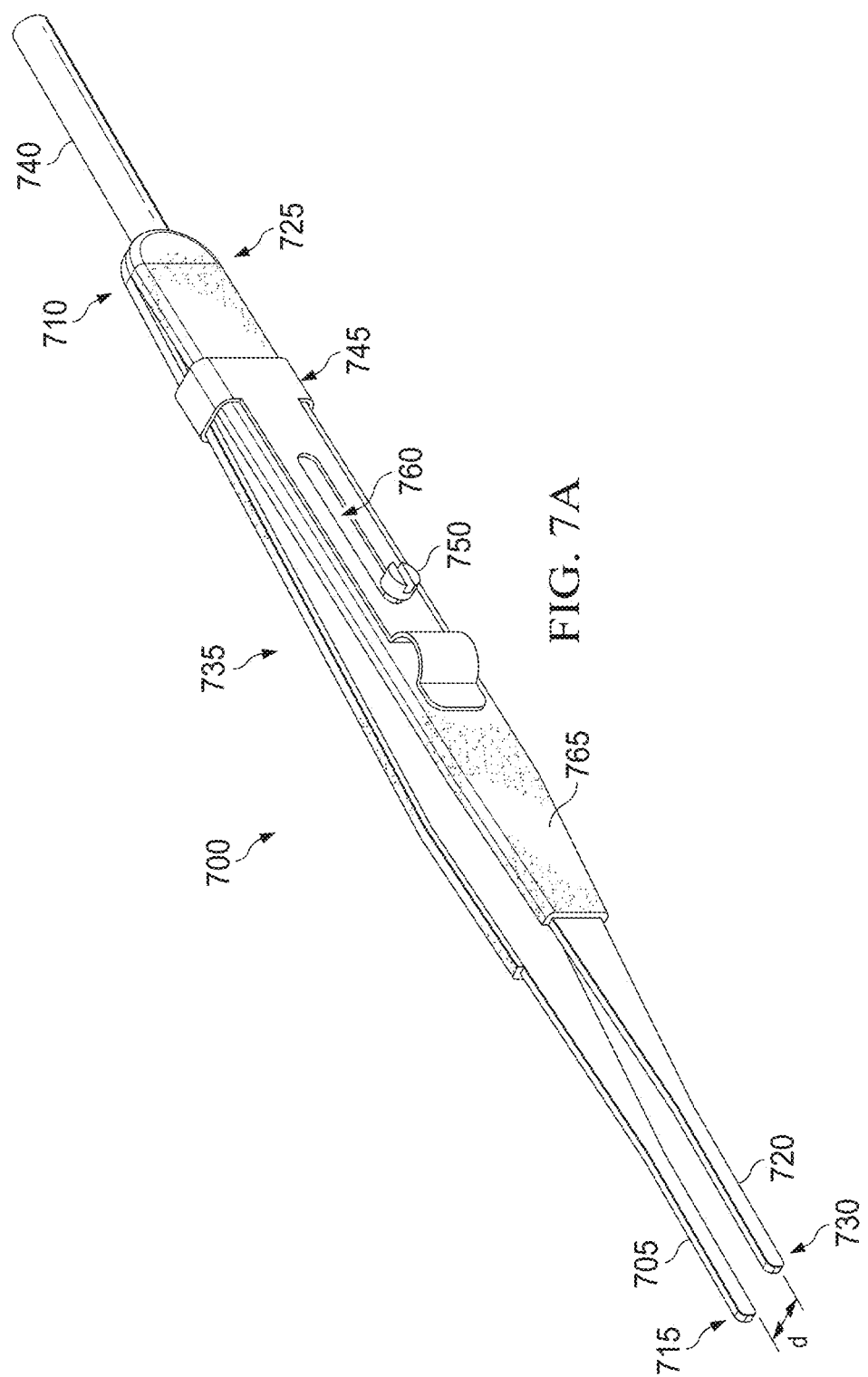
FIG. 7A is a perspective view of another embodiment of a removable tip for use with an electrosurgical device according to the present disclosure, shown with the removable tip in an open configuration.
Figure 7B:
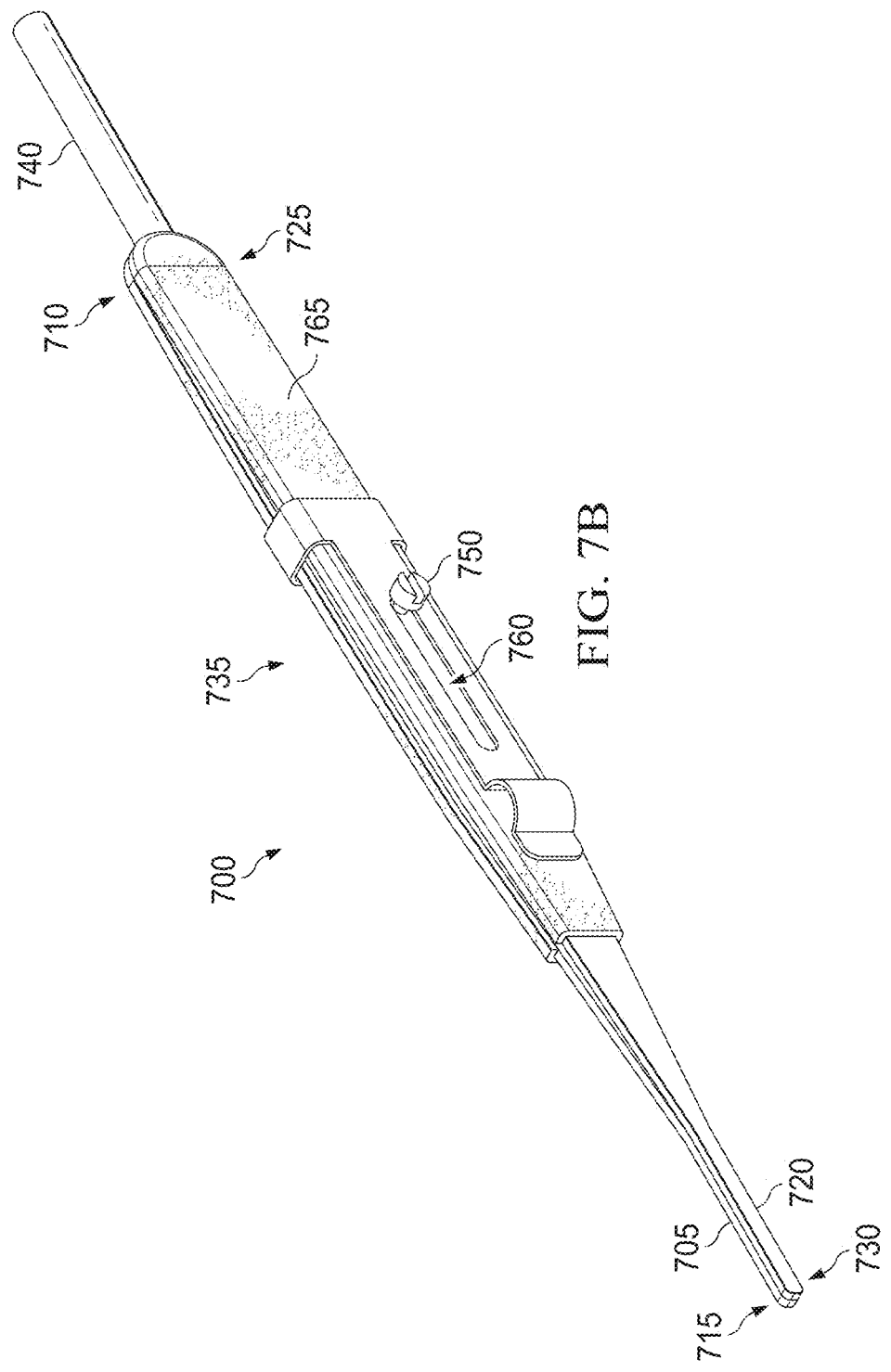
FIG. 7B is a perspective view of the removable tip shown in FIG. 7A, shown with the removable tip in a closed configuration.
Figure 7C:
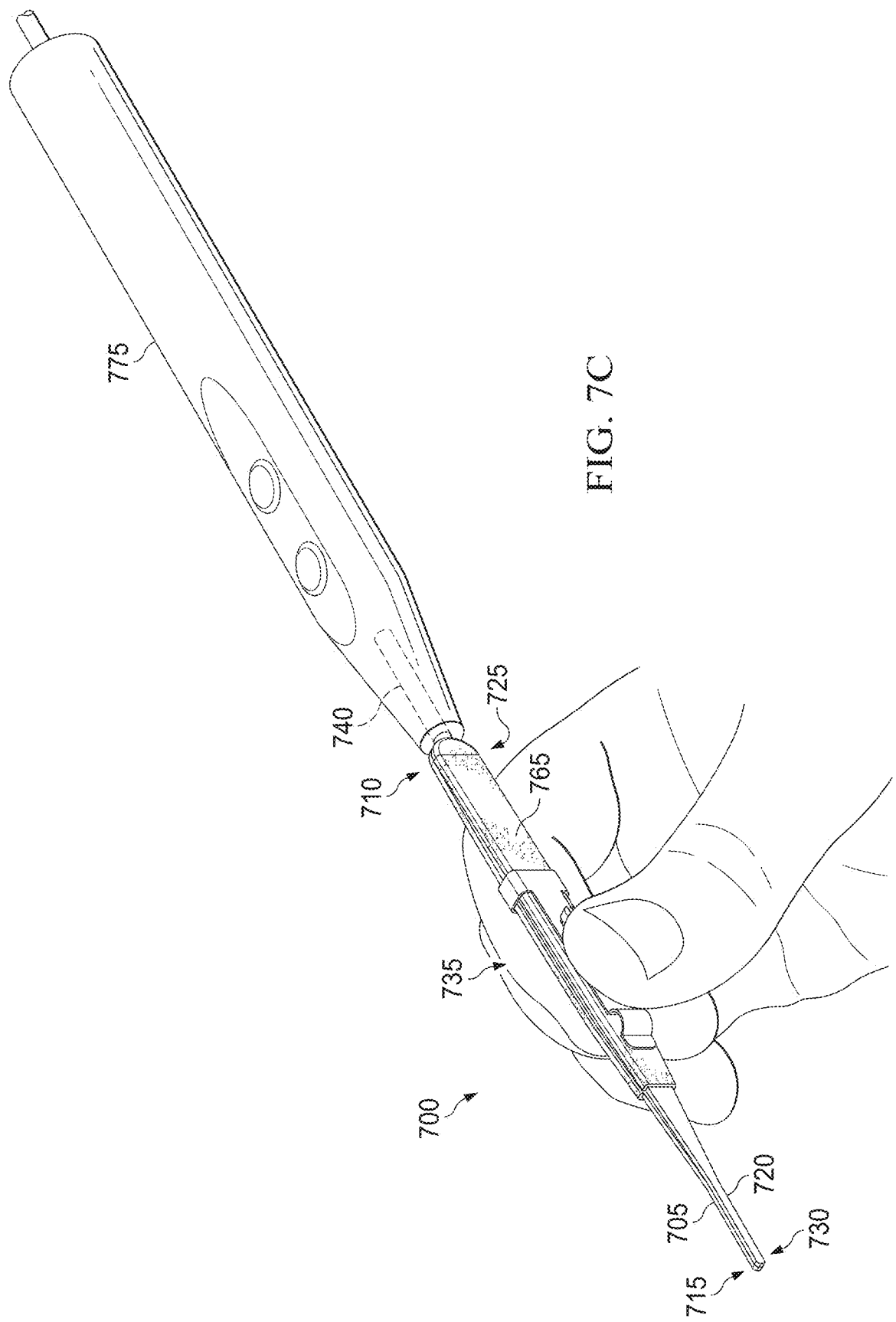
FIG. 7C is an environmental view of the removable tip shown in FIGS. 7A and 7B, shown with the removable tip in a closed configuration.

Referring now to FIGS. 7A-7C, there is shown yet another embodiment of a removable tip 700 coupled into a handheld electrosurgical unit 775 according to principles of the disclosure. The removable tip 700 may include a first tip member 705 having a proximal end 710 and a distal end 715. A second tip member 720 likewise has a proximal end 725 and a distal end 730. In some embodiments, at least one or both of the first tip member 705 and the second tip member 720 may include at least one electrically conductive surface near the distal ends 715 and 730 thereof. The first tip member 705 and second tip member 720 may be configured in some embodiments to move from a closed position to an open position, as discussed hereinabove and shown in FIG. 7A-7C. An insertion member 740 may extend from the removable tip neat the proximal ends 710 and 725, the insertion member 740 for inserting the removable tip 700 within an opening in the handheld electrosurgical unit 775.

In some embodiments, the removable tip may include an actuator 735 for moving the distal ends 715 and 730 of the first and second tip members 705 and 720 between a closed position and one or more open positions. In one embodiment, the actuator 735 may comprise part of the first tip member 705 and the second tip member 720. In one embodiment, the actuator 735 may include a locking mechanism 745, which in one embodiment includes a locking pin 750 positioned within a lateral slot 760. In some embodiments, the locking mechanism may be coupled around both the first and second tip members 705 and 720, and in some embodiments, near the proximal ends 710 and 725 thereof. In one embodiment, the first and second tip members 705 and 720 are in an "open position" as shown in FIG. 7A, which the distal ends 715 and 730 are separated by a distance d. To move the distal ends 715 and 730 toward a "closed position" a shown in FIG. 7B, axial pressure may be applied to the first and second tip members 705 and 720 and the locking mechanism 745 may be moved toward the distal ends 715 and 730. Once the distal ends 715 and 730 are closed together, in some embodiments, the pin 750 may be engaged to maintain the locking mechanism in a locked position. The pin 750 may be engaged by turning the pin 750 to a locked position, or in some embodiments may be locked in a compressed position.

Referring to FIG. 7C, there is shown an environmental view of the removable tip 700, shown with the actuator 735 engaged such that the distal ends 715 and 730 of the first and second tip members 705 and 720 are closed proximal each other. In this example, the actuator may include a coating or covering 765 at least on an outer surface. The coating 765 may comprise polymers, rubbers, plastics, and any other suitable material which may provide, in some embodiments, insulation from any electrical current running through the removable tip 700 and may also, in other embodiments, provide a non-slip grip, and/or comfort grip to a surgeon handling the removable tip 700.

In some embodiments, all of part of the removable tip 700 may include a non-stick coating which may be placed, in some embodiments, on at least the distal ends 715 and 730 of the first and second tip members 705 and 720 to reduce build-up of charred tissue thereon and also reduce a risk of thermal injuries. Several different types of non-stick coatings have been used or suggested for application to electrosurgical electrodes. Some of the different non-stick coatings or materials include fluorinated hydrocarbon materials, polytetrafluoroethylene (PTFE), perfluoroalkoxy, flexible silicone elastomers, ceramic composites, paralyene siloxane polymers, epoxy modified rigid silicone powder, silicone resin, and other suitable non-stick coatings.

Aspects of electrosurgical devices disclosed herein include the following:

A: A removable tip for use with an electrosurgical tool, the removable tip comprising a first tip member having a proximal end and a distal end; a second tip member having a proximal end and a distal end; an actuator for moving the first and second tip members between a closed position where the distal end of the first tip member and the distal end of the second tip member are proximate one another, and an open position where the distal end of the first tip member and the distal end of the second tip member are separated by a distance from one another, wherein the actuator includes a first actuating member comprising a portion of the first tip member and a second actuating member comprising a portion of the second tip member; and an insertion member coupled with the proximal ends of the first and second tip members, the insertion member for inserting the removable tip within an opening in an electrosurgical tool.

B: An electrosurgical tool, the electrosurgical tool system comprising a handheld electrosurgical unit, the handheld electrosurgical unit configured to be connected with an electrosurgical wall unit and including at least a first button to activate a cutting mode and a second button to activate a cauterizing mode; and a removable tip; the removable tip comprising a first tip member having a proximal end and a distal end; a second tip member having a proximal end and a distal end; an actuator for moving the first and second tip members between a closed position where the distal end of the first tip member and the distal end of the second tip member are proximate one another, and an open position where the distal end of the first tip member and the distal end of the second tip member are separated by a distance from one another, wherein the actuator includes a first actuating member comprising a portion of the first tip member and a second actuating member comprising a portion of the second tip member; and an insertion member coupled with the proximal ends of the first and second tip members, the insertion member for inserting the removable tip within an opening in the handheld electrosurgical unit.

Aspects A, B, and C may have one or more of the following additional elements in combination:

Element 1: wherein the insertion member is rotatable within the opening in the electrosurgical unit.

Element 2: wherein the actuator includes a coating on at least an outer surface of the first actuating member and the second actuating member;

Element 3: wherein the coating comprises a rubber;

Element 4: wherein the coating comprises a polymer;

Element 5: wherein axial pressure is applied the first actuating member and the second actuating member, pressing the first actuating member and second actuating member toward each other, in order to move the distal end of the first tip member and the distal end of the second tip member away from each other into the open position;

Element 6: wherein axial pressure is applied the first actuating member and the second actuating member, pressing the first actuating member and second actuating member toward each other, in order to move the distal end of the first tip member and the distal end of the second tip member toward and proximal to each other into the closed position;

Element 7: further comprising a locking mechanism for locking the removable tip in a closed position;

Element 8: wherein the locking mechanism is coupled about the first and second tip members and includes a locking pin positioned within a lateral slot;

Element 9: wherein the first and second tip members comprise at least one electrically conductive surface;

Element 10: wherein at least the distal ends of the first and second tip members include a non-stick coating;

Element 11: wherein the non-stick coating may include fluorinated hydrocarbon materials, polytetrafluoroethylene (PTFE), perfluoroalkoxy, flexible silicone elastomers, ceramic composites, paralyene siloxane polymers, epoxy modified rigid silicone powder, or silicone resin; and Element 12: wherein the distal ends of the first and second tip members are removably coupled with the actuator.

Those skilled in the art to which this application relates will appreciate that other and further additions, deletions, substitutions and modifications may be made to the described embodiments.

The invention claimed is:

1. A removable tip for use with an electrosurgical tool, the removable tip comprising:
    a first tip member having a proximal end and a distal end, wherein the first tip member is a single piece from the proximal end to the distal end;
    a second tip member having a proximal end and a distal end, wherein the second tip member is a single piece from the proximal end to the distal end and wherein the proximal end of the second tip member is directly coupled with the proximal end of the first tip member;
    an actuator for moving the first and second tip members between a closed position where the distal end of the first tip member and the distal end of the second tip member are proximate one another, and an open position where the distal end of the first tip member and the distal end of the second tip member are separated by a distance from one another, wherein the actuator includes a first actuating region comprising a portion of the first tip member and a second actuating region comprising a portion of the second tip member; and
    an insertion member directly coupled with the proximal ends of the first and second tip members, the insertion member for inserting the removable tip within an opening in the electrosurgical tool, wherein once the insertion member is fully inserted and positioned into the electrosurgical tool, the removable tip is rotatable within the opening in the electrosurgical tool while remaining fully inserted and positioned within the electrosurgical tool.

2. The removable tip according to claim 1, wherein the actuator includes a coating on at least an outer surface of the first actuating region and the second actuating region.

3. The removable tip according to claim 2, wherein the coating comprises a rubber.

4. The removable tip according to claim 2, wherein the coating comprises a polymer.

5. The removable tip according to claim 1, wherein the distal ends of the first and second tip members are configured to move away from each other into the open position when axial pressure is applied to both of the first actuating region and the second actuating region.

6. The removable tip according to claim 1, wherein the distal ends of the first and second tip members are configured to move toward and proximal to each other into the closed position when axial pressure is applied to both of the first actuating region and the second actuating region.

7. The removable tip according to claim 6, further comprising a locking mechanism for locking the removable tip in the closed position.

8. The removable tip according to claim 7, wherein the locking mechanism is coupled about the first and second tip members and includes a locking pin positioned within a lateral slot.

9. The removable tip according to claim 1, wherein the first and second tip members comprise at least one electrically conductive surface.

10. The removable tip according to claim 1, wherein at least the distal ends of the first and second tip members include a non-stick coating.

11. The removable tip according to claim 10, wherein the non-stick coating includes a material selected from the group consisting of fluorinated hydrocarbon, polytetrafluoroethylene (PTFE), perfluoroalkoxy, flexible silicone elastomers, ceramic composites, paralyene siloxane polymers, epoxy modified rigid silicone powder, or silicone resin.

12. The removable tip according to claim 1, wherein the distal ends of the first and second tip members each include an electrically conductive surface.

13. An electrosurgical tool, the electrosurgical tool comprising:
    a handheld electrosurgical unit, the handheld electrosurgical unit configured to be connected with an electrosurgical wall unit and including at least a first button to activate a cutting mode and a second button to activate a cauterizing mode; and
    a removable tip; the removable tip comprising:
        a first tip member having a proximal end and a distal end, wherein the first tip member is a single piece from the proximal end to the distal end;
        a second tip member having a proximal end and a distal end, wherein the second tip member is a single piece from the proximal end to the distal end and wherein the proximal end of the second tip member is directly coupled with the proximal end of the first tip member;
        an actuator for moving the first and second tip members between a closed position where the distal end of the first tip member and the distal end of the second tip member are proximate one another, and an open position where the distal end of the first tip member and the distal end of the second tip member are separated by a distance from one another, wherein the actuator includes a first actuating region comprising a portion of the first tip member and a second actuating region comprising a portion of the second tip member; and
        an insertion member directly coupled with the proximal ends of the first and second tip members, the insertion member for inserting the removable tip within an opening in the handheld electrosurgical unit, wherein once the insertion member is fully inserted and positioned into the handheld electrosurgical unit, the removable tip is rotatable within the opening in the handheld electrosurgical unit while remaining fully inserted and positioned within the handheld electrosurgical unit.

14. The electrosurgical tool according to claim 13, wherein the actuator includes a coating on at least an outer surface of the first actuating member and the second actuating member.

15. The electrosurgical tool according to claim 13, wherein the distal ends of the first and second tip members are configured to move away from each other into the open position when axial pressure is applied to both of the first actuating region and the second actuating region.

16. The electrosurgical tool according to claim 13, wherein the distal ends of the first and second tip members are configured to move toward and proximal to each other into the closed position when axial pressure is applied to both of the first actuating region and the second actuating region.

17. The electrosurgical tool according to claim 16, further comprising a locking mechanism for locking the removable tip in the closed position.

18. The electrosurgical tool according to claim 17, wherein the locking mechanism is coupled about the first and second tip members near the proximal ends thereof and includes a locking pin positioned within a lateral slot.

* * * * *